United States Patent [19]

Gray et al.

[11] Patent Number: 4,680,177
[45] Date of Patent: Jul. 14, 1987

[54] PROCESSES FOR THE PRODUCTION OF BLOOD PRODUCTS

[75] Inventors: Charles R. W. Gray, Forest Row; Neville Crawford, St. Albans, both of England

[73] Assignees: Trustees of the Garfield Weston Trust for Research into Heart Surgery; The Royal College of Surgeons of England; British Postgraduate Medical Federation, all of London, England

[21] Appl. No.: 579,905

[22] PCT Filed: Apr. 28, 1983

[86] PCT No.: PCT/GB83/00127
§ 371 Date: Jan. 3, 1984
§ 102(e) Date: Jan. 3, 1984

[87] PCT Pub. No.: WO83/03830
PCT Pub. Date: Nov. 10, 1983

[30] Foreign Application Priority Data

Apr. 28, 1982 [GB] United Kingdom ................. 8212306

[51] Int. Cl.$^4$ .................... A61K 35/14; A61K 35/16; A61K 35/18; A61K 35/28
[52] U.S. Cl. .................................................. 424/101
[58] Field of Search ........................................ 424/101

[56] References Cited

U.S. PATENT DOCUMENTS 2,196,199 4/1940 Dyckerhoff ..................... 424/101
2,532,348 12/1950 Szent-Gyorgyi .................. 424/101

OTHER PUBLICATIONS

Sole—Chem. Abst., vol. 55 (1961), p. 4689d.
Shulman et al.–Chem. Abst., vol. 47 (1953), pp. 11280i to 11281a.
Menghini–Chem. Abst., vol. 43(1949), p. 4378a.

Primary Examiner—Sam Rosen
Attorney, Agent, or Firm—Owen, Wickersham & Erickson

[57] ABSTRACT

Blood products and derivatives, such as procoagulants—e.g. Factor VIII and prothrombin—plasma proteins, immunoglobulin and complement growth factors and various leucocytes, are obtained from shed blood or its tissue precursor, bone marrow, that has been anticoagulated by the use of a neutral salt that does not bind calcium ions. The preferred anticoagulants are salts containing the divalent ions calcium, magnesium, barium or strontium. Salts of calcium and magnesium are especially preferred because of their relatively lower toxicity, the salt of choice being a magnesium salt, for instance magnesium chloride, because magnesium salts exhibit the required anticoagulating action at levels compatible with retention of normal ionic strength and osmolarity. The toxicity of the neutral salt is eliminated by its removal.

14 Claims, No Drawings

PROCESSES FOR THE PRODUCTION OF BLOOD PRODUCTS

This invention concerns blood products and the processes of their production from mammalian blood or its precursor tissue, bone marrow.

Whole blood is an extremely complex biological fluid and its components undergo a variety of changes in response to changes in the blood environment: coagulation or clotting is one phenomenon that is normally exhibited by shed blood and is the consequence of various complex changes in the blood constituents in response to an environmental change. The clotting mechanism is imperfectly understood but is believed to depend upon the presence in the whole blood of certain constitutents or Factors such as prothrombin and Factors V, VIII and IX and other blood coagulant proteins.

The prevention or delaying of clotting is accomplished by the use of anticoagulants, while clotting can be induced, e.g. in the treatment of haemophilia, by administration of whole blood containing the clotting factors or by the administration of a blood fraction or extract believed to contain the clotting factors.

Whole blood and its components and derivatives have many uses in medical science and its application. All procédures involving the use of shed blood, whether for subsequent transfusion or for processing to obtain blood products, involve an initial treatment to inhibit the clotting mechanism and the literature is replete with descriptions of various materials useful as anticoagulants. However, because for at least one hundred years it has been almost universally believed that the presence of calcium ions, in free or appropriately bound form, in blood was a requirement for coagulation, the anticoagulant materials most commonly used have been those designed to prevent calcium exerting its coagulating effect, as by binding free calcium ions to some structure that inhibits their coagulating action in the blood. Thus for example salts such as fluorides, oxalates, citrates and salts of ethylenediamine tetraacetic acid (EDTA) are to be found in conventional anticoagulants.

There have been a few reports in the literature of the anticoagulant effect of certain neutral salts which do not bind calcium ions, but in general, because this is contrary to conventional wisdom, the use of such neutral salts as anticoagulants has not been explored to any signficant extent in practice.

Thus, for example, Horne in *J. Physiology* (1896) 19 356/371 reported that blood coagulation was inhibited by the addition of ionic barium, strontium or calcium, with effectiveness in that order, and that the inhibition was reversed by dilution of the anticoagulated blood with water. Horne also reported that the coagulation-inhibiting effect of the divalent cations was enhanced by the presence of sodium chloride and potassium chloride.

Zarday in *Folio Haematologica* (1934) 52 33-39 established that divalent calcium had a specific anticoagulant effect and that its action was not just due to an increase in ionic strength.

Greville & Lehmann in *J. Physiology* (1944) 103 175-184 established a true antagonism between calcium and magnesium ions. They showed that calcium ions in a low concentration, less than 5 mM, antagonises the anticoagulant effect of other divalent cations such as strontium, barium and magnesium and reported that the anticoagulation of blood by magnesium chloride "may possibly be of practical value for the storage of blood". They describe the addition of two parts of blood to one part of M/7 magnesium chloride (143 mM) so that the anticoagulated blood exhibits a magnesium chloride concentration of 47.7 mM.

Lovelock & Porterfield in *J. Biochem.* (1951) 50 415 showed that below a total ionic strength of 0.01, plasma does not clot. The optimal ionic strength for coagulation is 0.03 and high ionic strength inhibits coagulation.

Zucker in a paper from the 1960 Symposium in Philadelphia, U.S.A. on "Metal-binding in Medicine" mentions that adding magnesium chloride to EDTA anticoagulated plasma preserves Factor V and Factor VIII. However she does not mention anticoagulation ab initio with magnesium chloride for this purpose, although she makes it clear that she was aware that high concentration of calcium chloride or magnesium chloride can inhibit coagulation, as reported by earlier workers.

In view of the conventional wisdom that calcium binding or sequestering is the mechanism of choice in a practical anticoagulant, the few reports in the literature of anticoagulant activity by neutral salts that do not bind calcium have hitherto been dismissed as academic curiosities of no practical importance.

We have now discovered that contrary to the generally held beliefs as discussed above, the use of suitable neutral salts for the anticoagulation of freshly shed blood, without calcium-binding materials such as conventional anticoagulants being present, greatly increases the length of time after which useful blood components or their derivatives can be extracted from the blood. It also appears that by applying normal processing techniques to the anticoagulated shed blood, after the customary short delay, certain useful blood products can be obtained in higher effective yields than hitherto. It appears that similar unexpected advantages are obtainable by anticoagulation of bone marrow with the same agents.

We can offer no proven explanation for these findings but believe that because the neutral salts do not affect the ionic environment of certain blood proteins in the way that calcium-binding anticoagulants may do so, the proteins in question are not subject to the degradation or other effects that could flow from the ionic environmental change consequent upon the presence of calcium-binding anticoagulants.

Thus in its broadest aspect the present invention provides a process for the production of useful products from anticoagulated shed blood or bone marrow that is characterised by the use as the anticoagulant of a neutral salt which does not bind calcium ions.

A variety of neutral salts may be used. However we prefer to use neutral salts containing one or more of the divalent ions calcium, magnesium, barium and strontium, calcium and magnesium being preferred as being least toxic when the blood or bone marrow product or derivative may have to be used clinically; and, because it exhibits the required anticoagulating effect with the least effect upon the ionic strength and osmolarity of blood as discussed in more detail below, we prefer to use a neutral salt containing magnesium ions, such as magnesium chloride. The divalent ions may be supplemented by the presence of sodium and/or potassium ions.

Suitable concentrations of anticoagulant are such as to provide the equivalent of a 10 to 500 mM solution of the neutral salt in anticoagulated blood. However we prefer the blood anticoagulant concentration to be equivalent to a 15 to 250 mM solution, or more preferably a 16 to 100 mM solution, of neutral salt, in the anticoagulated blood.

When, as is preferred, the neutral salt is a magnesium salt, the anticoagulated blood magnesium salt content is preferably such as to be equivalent to a solution in the range 18 to 50 mM, and is most desirably equivalent to a solution of about 25 mM.

If the anticoagulant neutral salt contains calcium ions, a rather higher concentration of such ions, in anticoagulated blood, is required to achieve the same inhibition of coagulation as compared with the use of an anticoagulant containing magnesium ions.

The anion associated with the cation of the neutral salt will normally be such as to provide a water soluble neutral salt. Suitable anions include halides, nitrate, acetate and the like, the preferred anion being chloride.

The concentration of neutral salt (divalent cation) present, with or without the addition of monovalent ions, may vary according to the particular purpose for which the anticoagulated blood or bone marrow is to be employed, for example the isolation of clotting factors or platelets or leucocytes.

The skilled worker will appreciate that blood anticoagulated and preserved by neutral salts is qualitatively different from conventionally anticoagulated and preserved blood because the high levels of neutral salt in the blood preclude its direct clinical use as whole blood in humans, owing to the toxic effects of such high levels of neutral salt ions, for example, calcium or magnesium ions. However, prior to further use or processing of the anticoagulated and preserved blood, the toxic levels of such ions may if required be reduced by treatment of the blood, for example by passage through an ion exchange resin or by dialysis, which will selectively remove the ions to below their toxic levels. Certain subsequent procedures employed for the isolation of proteinaceous products or cells from the blood can result in concentrations of ions from the neutral salt in the product below their toxic levels. For example, platelets isolated from anticoagulated and preserved blood or plasma may be simply washed with aqueous sodium chloride solution to reduce the levels of ions of the neutral salt to below toxic levels, after which the platelets may be reinfused into the body.

Mammalian blood anticoagulated and preserved in the manner of the invention will be very useful in the preparation of blood products. Most aptly the blood is human blood, pig blood or other animal blood. Human blood is favoured because of the lower immunogenic potential of the end products but pig or other blood may be used for such materials as cryoprecipitate (also known as Factor VIII concentrate), Antihaemophillic Factor (AHF, also known as Factor VIII) and prothrombin, in view of its greater availability.

The blood is most aptly removed from the mammalian donor by conventional means and may be collected in a flexible plastic "blood pack" which has been precharged with an aqueous solution containing a sufficient amount of neutral salt to provide an appropriate concentration of ions when admixed with the blood. Conventionally the container will receive up to 450 ml of blood, which is also known as a unit of blood, and will be mixed with a suitable volume of an aqueous solution containing the neutral salt, to provide the required composition of anticoagulated blood. The salt may alternatively be present as a dry solid, in suitable amount, in a container into which shed blood is collected.

The collection and preservation of the whole blood is performed without the addition of calcium ion-binding or sequestering anticoagulants, such as Citrate-Phosphate-Dextrose (CPD) or Acid-Citrate-Dextrose (ACD), oxalates, fluorides, ethylenediamine tetraacetic acid and the like, but heparin or hirudin-like substances may be used in conjunction with a neutral salt anticoagulant.

It is believed by some authorities to be advantageous when isolating certain cellular or proteinaceous blood fractions, for example Antihaemophillic factor (AHF), plasma proteins, leucocytes or platelets, first to separate the blood plasma from the other cellular components of the blood such as red cells. This may be performed on whole blood which has been admixed with an aqueous solution of neutral salt as hereinbefore described. Conventional processes of centrifugation or filtration may be used in which the plasma fraction will contain the neutral salt after the desired separation from any of the cellular components or may be immediately treated to reduce the level of neutral salt.

An important component of whole blood and blood plasma which is present in these fluids in small amounts is Anti-haemophillic Factor or Factor VIII. Several processes for isolating this Factor from whole blood and plasma are known. However, it is difficult to isolate because of its low concentration in plasma, the difficulty in separating it from other plasma proteins, such as fibrinogen and its ready susceptibility to denaturation by heat, freezing and continued storage. One preferred process involves a cryoprecipitation step, that is by freezing plasma to low temperature and then thawing at 0° to 4° C., a precipitate highly enriched in Factor VIII (known as cryoprecipitate or Factor VIII concentrate) is obtained. However it has been found that the yield of cryoprecipitate has a coagulant activity which is low and highly variable when this method is used on whole blood or blood plasma anticoagulated in a conventional manner. It has now been found that whole blood or blood plasma which has been anticoagulated and preserved with neutral salt as hereinbefore described may be processed by cryoprecipitation to give a potency or Factor VIII coagulant activity which is at least equal to that obtained from whole blood preserved with ACD and CPD anticoagulants, and also allows the plasma to be stored before processing for a longer period, up to 4 days, whilst still providing a high yield of Factor VIII concentrate after processing, as compared to ACD or CPA preserved blood.

Conventionally the cryoprecipitate is isolated as a slurry and is frozen and stored at $-18°$ C. The yield of coagulant activity in conventionally isolated cryoprecipitate, is low in relation to the plasma from which the cryoprecipitate is derived, so that to provide an effective dose a large volume of reconstituted cryoprecipitate must be infused into the patient. To overcome this disadvantage processes have been devised to further purify Factor VIII to increase the specific coagulant activity. Such methods of further purifying Factor VIII may be usefully employed on blood or blood plasma anticoagulated and preserved with neutral salt as herein described. Suitable methods include fractionation by solvent extraction from fresh or frozen plasma.

Other useful components of whole blood include the leucocytes or white cells. Different types of leucocytes include macrophages, neutrophils, eosinophils, basophils, lymphocytes and the like. Neutrophils are, for example, useful in the treatment of neutropenia: that is, they will increase the low counts of white blood cells which may occur following cancer chemotherapy, irradition or drug treatment and the like. Leucocytes without preservation must be used within 5 to 6 hours because of their instability at room temperature. Low temperature storage, when these products have been obtained by conventional methods, does not greatly enhance their period of viability. British Pat. No. GB-A-1,581,718 describes several conventional methods of isolating leucocytes from whole blood and how their viability may be maintained for a period of several days by storing them in the presence of a large number of amino acids, inorganic salts, antibiotics and heat-inactivated foetal calf serum. It has now been found that by isolating leucocytes from whole blood which has been anticoagulated and preserved by the presence of neutral salt, especially one containing calcium or magnesium ions, certain functional properties may be extended from under 24 hours to up to 5 days and even 7 days. The leucocytes may be isolated by conventional means from whole blood containing neutral salt. Subjecting the isolated leucocytes to chemotaxis, random mobility, phagocytosis (candida killing), staphylocoecal killing and glass adhesion demonstrates that the cells remain functionally competent for 5-7 days instead of the normal 24 hours.

Blood platelets after storage for a few hours, and then infused, do not express their full haemostatic properties. As a result bleeding disorders and certain thrombocytopenias must be treated with freshly prepared platelet suspensions. It has now been found that platelets in suspension, when isolated from whole blood which has been anticoagulated and preserved by the presence of neutral salt, especially when containing calcium or magnesium ions, maintain their morphology and remain discoid for longer periods than those normally isolated platelets in suspension. The plasma content of platelet release products, for example, $\beta$-thromboglobulin is lower than conventionally anticoagulated blood or anticoagulated blood using ACD and platelet release inhibitors such as prostaglandin E, and phosphodiesterase inhibitors.

In most of our later studies, of the properties of blood and plasma anticoagulated and preserved by the use of neutral salts, more emphasis has been placed upon the use of magnesium salt rather than calcium salt as the anticoagulant because earlier studies described below had shown that magnesium anticoagulation could be effected at lower concentrations of the salt than calcium anticoagulation. The lower the concentration one can use then the less the effect upon ionic strength and osmolarity of the blood. Maintenance, as far as possible, of the normal blood ionic strength and osmolarity is better for both cellular and plasma constitutents.

The early studies may be summarised by the following experiments.

From an initial 500 mM solution of $MgCl_2$ a series of solutions of different dilutions were made. $MgCl_2.6H_2O$ has a molecular weight of 202.3, so 101.15 g dissolved in distilled water and made up to 1,000 ml gives a 500 mM solution. Aliquots of this 500 mM solution were diluted to give solutions of 450, 400, 350, 300, 250, 200, 150, 100 and 50 mM $MgCl_2$ respectively.

Similar solutions made by dilution of 600 mM $CaCl_2$ (Mol. wt. $CaCl_2 2H_2O = 146$, 87.6 gm to 1000 ml for 600 mM).

Blood/anticoagulant mixtures consisting of nine volumes blood to one volume anticoagulant were made up throughout the dilution range, using both $Mg^{2+}$ and $Ca^{2+}$ anticoagulant solutions. These mixtures were placed in parafilm sealed tubes that were examined visually for signs of clotting by regular inversion of the tubes. All the tubes were maintained at room temperature. (Rt°, ca. 19°-20° C.). All experiments were duplicated and the results of each pair (A and B) are tabulated below.

| mM $CaCl_2$ * | TIME TO COMPLETE CLOTTING (min.) | | mM $MgCl_2$ * | TIME TO COMPLETE CLOTTING (min.) | |
|---|---|---|---|---|---|
| | A | B | | A | B |
| 0 | 17 | 18 | 0 | 13 | 17 |
| 5 | 35 | 35 | 5 | 34 | 25 |
| 10 | 45 | 45 | 10 | 65 | 65 |
| 20 | 65 | 60 | 15 | 123 | 105 |
| 30 | 104 | 114 | 20 | 238 | 205 |
| 40 | 137 | 150 | 25 | NO CLOTTING AT 12 & 24 HOURS | |
| 50 | 253 | 253 | 30 | | |

*These concentrations are based upon 1/10 dilution of anticoagulant in the whole blood. In fact later studies revealed little binding or entry of the metal ion into cells and therefore, dependent upon the volume the cells occupy in the blood, the actual molarities in the plasma will be higher by a factor of approximately 1.5. (The factor is exactly 1.5 if the packed cell volume (PCV) is 40%:

i.e. $\frac{60}{40} = 1.5$).

In practice the cell volume percentage varies and is significantly lower in females, so that in female blood there would be lower plasma levels of divalent metal ion.

Other similar studies have confirmed that with a large number of different donors, anticoagulant levels of 25 mM $MgCl_2$ (theoretical as above discussed) safely ensure no clotting for up to six days.

$CaCl_2$ will anticoagulate successfully at this level, but clotting is always seen by 12-24 hours and sometimes is detectable earlier. $CaCl_2$ at a concentration greater than 60 mM is required to anticoagulate for longer than 2 days. $MgCl_2$ is effective at half the concentration of $CaCl_2$ for a given anticoagulating action.

As noted $MgCl_2$ solutions have advantages in relation to ionic strength and osmolarity in the anticoagulated blood. Thus blood normally has ionic strength ($\mu$) of about 0.15 and osmolarity of about 300 milliosmols.

Ionic strength ($\mu$) is defined as half the sum of all the terms obtained by multiplying the concentration of each ion in the solution by the square of its valency.

For example, $MgCl_2$ dissociates in solution to give $Mg^{2+}$ and $2Cl'$, so that for 250 mM $MgCl_2$, the ionic strength approximates to 0.210. This total is significantly higher than the value $\mu = 0.15$ for blood alone.

However, if for example 100 mM $MgCl_2$ ($\mu = 0.30$) was used at an anticoagulant/blood ratio of 1:3, $\mu$ of the mixture is approximately 0.113. Although this appears to be lower than desirable, in fact $\mu$ is higher in the plasma for the reasons discussed above.

Osmolarity is defined as the product of the molarity multiplied by the number of ionisable species. For example, NaCl gives two species, $Na^+$ and $Cl'$, whereas $MgCl_2$ give $Mg^{2+}$ plus $2Cl'$, a total of three ionisable species.

The osmolarity of 250 mM $MgCl_2$ is therefore 750 milliosmolar.

The normal osmolarity of blood is 300 milliosmolar, so that:

| | |
|---|---|
| Blood diluted 9 → 10 | 270 milliosmolar |
| Anticoagulant diluted 1 → 10 | 75 milliosmolar |
| Total osmolarity of mixture | 345 milliosmolar |

However, for 100 mM $MgCl_2$ and 1 to 4 dilution with blood, the mixture has an osmolarity of 300 milliosmoles, the same as blood alone.

Atomic Absorption Analyses of Blood Anticoagulated with Magnesium

The normal levels of $Ca^{2+}$ and $Mg^{2+}$ in plasma are about 2–2.5 mM and 1 mM respectively.

Whole blood assays of $Ca^{2+}$ and $Mg^{2+}$-ashed samples.

Two samples anticoagulated with 250 mM $MgCl_2$ at ratio 1:9 by volume

| | CALCIUM | | MAGNESIUM | |
|---|---|---|---|---|
| SAMPLES | µg ml$^{-1}$ | mM | µg ml$^{-1}$ | mM |
| Whole blood A | 62.3 | 1.6 | 835 | 34.4* |
| Whole blood B | 50.3 | 1.3 | 767 | 31.6* |

*Higher than theoretical 25 mM, suggesting little binding to cells and plasma. The divalent ion concentration relates to the packed cell volume (PCV)

This study was repeated with blood separated into plasma and cells by centrifugation (2500 rpm for 20 mins).

Two blood samples anticoagulated with 250 mM $MgCl_2$ at ratio 1:9 by volume.

| | CALCIUM | | MAGNESIUM | |
|---|---|---|---|---|
| SAMPLES | µg ml$^{-1}$ | mM | µg ml$^{-1}$ | mM |
| Plasma A | 93 | 2.3 | 902 | 37.1 |
| Packed cells A (not washed) | 5.1 | 0.13 | 40.5 | 1.7 |
| Plasma B | 89 | 2.2 | 1148 | 47.3 |
| Packed cells B (not washed) | 5.3 | 0.13 | 37.9 | 1.6 |

This study was again repeated, with six blood samples anticoagulated with 250 mM $Mg^{2+}$.

Bloods separated into plasma and packed cell fractions.

Plasma analysed for $Ca^{2+}$ and $Mg^{2+}$ directly.

Packed cells added to 0.154M NaCl to give original blood volume, mixed and centrifuged again (2500 rpm for 20 mins).

Supernatant = washings. Pellet = washed cells (for conversion Ca = 40, Mg = 24.3).

The results are presented in the following Table.

| | | CALCIUM | | | MAGNESIUM | | |
|---|---|---|---|---|---|---|---|
| SAMPLES | | µg ml$^{-1}$ | mM | Mean (mM) | µg ml$^{-1}$ | mM | Mean (mM) |
| PLASMA | 1 | 87.3 | 2.2 | | 730.0 | 30.0 | |
| | 2 | 90.8 | 2.3 | | 695.8 | 28.6 | |
| | 3 | 87.0 | 2.2 | | 639.7 | 26.3 | |
| | | | | 2.2 | | | 27.9 |
| | 4 | 84.1 | 2.1 | | 629.8 | 25.9 | |
| | 5 | 94.8 | 2.4 | | 849.8 | 35.0 | |
| | 6 | 89.1 | 2.2 | | 531.5 | 21.9 | |
| WASHINGS | 1 | 12.0 | 0.30 | | 103.4 | 4.3 | |
| | 2 | 11.5 | 0.29 | | 84.4 | 3.5 | |
| | 3 | 14.2 | 0.36 | | 103.6 | 4.3 | |
| | | | | 0.31 | | | 3.8 |
| | 4 | 11.5 | 0.29 | | 84.5 | 3.5 | |
| | 5 | 11.2 | 0.28 | | 87.2 | 3.6 | |
| | 6 | 15.2 | 0.38 | | 89.7 | 3.7 | |

| | | A* | B* | A* | B* | A* | B* | A* | B* |
|---|---|---|---|---|---|---|---|---|---|
| WASHED PACKED CELLS | 1 | 5.7 | 5.2 | 0.14 | 0.13 | 27.3 | 26.8 | 1.1 | 1.1 |
| | 2 | 5.6 | 4.5 | 0.14 | 0.11 | 23.1 | 23.0 | 1.0 | 0.9 |
| | 3 | 4.2 | 4.5 | 0.11 | 0.11 | 25.5 | 25.4 | 1.0 | 1.0 |
| | 4 | 5.4 | | 0.14 | | 25.2 | 27.1 | 1.0 | 1.1 |
| | 5 | 4.8 | | 0.12 | | | 26.7 | 1.1 | |
| | 6 | 3.9 | | 0.10 | | | 23.8 | 1.0 | |
| | | Mean (n = 6) = | | 0.12 mM | | Mean (n = 6) = | | 1.0 mM | |

*Duplicate results

CONCLUSION

There appears to be little or no binding of $Mg^{2+}$ to the cellular contents of blood with 250 mM $MgCl_2$ used as anticoagulant. Because the washings contain 3–4 mM $Mg^{2+}$, simple deposition of cells by centrifugation and resuspension in saline is inadequate to reduce the magnesium content to safe clinical levels.

Atomic absorption analyses of cryoprecipitates

Two samples of cryoprecipitate from blood anticoagulated conventionally with citrate phosphate dextrose (CPD) were compared with one sample from blood anticoagulated with 250 mM $MgCl_2$ 1:9 by volume, in determinations of calcium and magnesium.

CPD anticoagulated

CRYO A 0.67 mM $Mg^{2+}$, 2.32 mM $Ca^{2+}$.
CRYO B 0.74 mM $Mg^{2+}$, 1.98 mM $Ca^{2+}$.

$MgCl_2$ anticoagulated 38.3 mM $Mg^{2+}$, 2.07 mM $Ca^{2+}$.

This study was repeated for plasma and red cells to determine $Mg^{2+}$ and $Ca^{2+}$.

Blood was anticoagulated with 250 mM $MgCl_2$ 1:9 by volume: plasma was prepared by centrifugation (2500 rpm for 20 mins) and the packed cells resuspended to original blood volume with saline.

| | CALCIUM | | MAGNESIUM | |
|---|---|---|---|---|
| | µg ml$^{-1}$ | mM | µg ml$^{-1}$ | mM |
| Plasma A | 104.5 | 2.6 | 778 | 32.0 |
| Resuspended cells A | 1.6 | 0.04 | 44.3 | 1.82 |

-continued

|  | CALCIUM | | MAGNESIUM | |
|---|---|---|---|---|
|  | µg ml$^{-1}$ | mM | µg ml$^{-1}$ | mM |
| Plasma B | 74 | 1.85 | 726 | 29.8 |
| Resuspended cells B | 1.85 | 0.05 | 36.8 | 1.51 |

Preservation of certain coagulant factors in plasma (F.VIII, F.V. and F.IX)

Parallel determinations were made on various plasmas from duplicate CPD-anticoagulated bloods and compared with plasmas from bloods anticoagulated with 250 mM MgCl$_2$ 1:9 by volume.

Analyses of fresh plasma (within 1 hour of donation) showed no significant differences between both anticoagulants, both of which seem to be effective.

|  | UNCORRECTED INTERNATIONAL UNITS F.VIII/ml. diluted blood 9 to 10. | |
|---|---|---|
| PLASMA (DONOR) | CPD | MgCl$_2$ |
| 1. (N.C.) | 0.56 | 0.53 |
| 2. (A.L.B.) | 0.82 | 0.76 |
| 3. (C.R.W.G.) | 1.35 | 1.80 |

These plasmas were also stored for 1 day at +4° C. and the assays repeated. No significant differences were noted as between the 1 day old and the fresh samples.

Comparison F.VIII assays (1 stage test) N.I.B.S.C.

|  | Concentration theoretical |
|---|---|
| A. Blood N.C. 1 ml 250 mM MgCl$_2$ + 9 ml blood | 25 mM |
| B. Blood N.C. 1 ml 100 mM MgCl$_2$ + 3 ml blood | 25 mM |
| Procedure. Plasma separated by centrifuging (2500 rpm for 20 mins) and divided into aliquots. | |

Samples A$_o$ and B$_o$ snap frozen with solid CO$_2$ and stored at −20° C.

A series samples A$_2$ and A$_6$ stored for 2 days and 6 days respectively at room temperature, Rt° and then snap frozen.

B series samples B$_2$ and B$_6$ stored for 2 days and 6 days respectively at +4° C., then snap frozen.

Factor VIII results were corrected for dilution with the 100 mM MgCl$_2$ anticoagulant:

* i.e. for dilution of blood 3→4, correction Factor is (4/3×9/10)=1.2

|  | (Corrected I.U.F.VIII for dilution) | | |
|---|---|---|---|
| Assays at N.I.B.S.C. | ZERO TIME | 2 days | 6 days |
| ROOM TEMP STORAGE | | | |
| Mg. 100 mM (A) | 0.75 | 0.34 | 0.54 |
| 250 mM (B) | 0.50 | 0.28 | 0.26 |
| +4° STORAGE | | | |
| 100 mM (A) | 0.75 | 0.30 | 0.30 |
| 250 mM (B) | 0.50 | 0.27 | 0.23 |

CONCLUSION

The more diluted blood (anticoagulated with 100 mM Mg) had better F.VIII potency at zero time than the samples anticoagulated with 250 mM Mg. This difference was not, however, so marked at 2 and 6 days.

Measurements of β-thromboglobulin in plasma

β-Thromboglobulin (βTG) is a protein (glycoprotein) stored in platelet granules. It is released in response to haemostatic stimuli, so that its amount in plasma reflects any platelet activation. Since βTG can be released from platelets during blood collection a cocktail is conventionally used to avoid artifactual levels in plasma. The cocktail contains inhibitors for platelet activation, e.g. Prostaglandin E$_1$, EDTA and theophylline.

The normal range for βTG in plasma is 15–50 nanograms/ml. (Four large series gave range 24–28 as mean values, with 90% within 52 ng/ml-wide scatter band). All series used CPD or ACD as anticoagulant.

Assays were made with Amersham Radioimmunoassay Kit.

| CODE NO. | PLASMA βTG ng/ml | CODE NO. | PLASMA βTG ng/ml |
|---|---|---|---|
| N.C. 1 | 16 | D.I.H.S. 5 | 15 |
| C.H.E. 2 | 13 | INS. CO. 6 DONOR | 22 |
| C.R. 3 | 0* | INS. CO. 7 DONOR | 0 |
| G.S. 4 | 11 | INS. CO. 8 DONOR | 17 |

These results seem at least as good, if not better, than with the cocktail. Zero values (*) reflect a result below the limits of detection with the kit. (ca. 5–8 ng/ml) which in later studies are reported as being below 10 /ng/ml. Means of above values: 11.7 ng/ml Range 0–22 ng/ml.

Comparison βTG plasma various anticoagulants.
Amersham Kit

| βTG ng/ml (Blood/anticoagulant ratio 1:9) | | |
|---|---|---|
| 200 mM MgCl$_2$ | <10 | <10 = below the limits of detection with the assay kit |
| 300 mM MgCl$_2$ | <10 | |
| 400 mM MgCl$_2$ | <10 | |
| 500 mM CaCl$_2$ | 27 | |
| 0.38% Na citrate | 18 | |
| " | 17 | |
| ACD | 31 | |
| " | 35 | |
| CPD | 29 | |
| " | 27 | |
| EDTA PGE$_1$ | <10 | |
| + Theophylline | <10 | |
| EDTA ONLY 0.15% | 18 | |
| | 18 | |

Platelet morphology and function

Morphology

Platelets are the smallest and most sensitive cells in the circulation. In normal circulation they are discoid (lentiform shape) and when activated change from discs to spheres and form long processes, pseudopodia, which interact with damaged vessel walls and other platelets.

The disposition and integrity of the intracellular features is also disturbed, e.g. the microtubule ring disappears and granules release haemostatic and procoagulant factors.

Transmission and scanning electron microscopy has been used to examine the morphology of platelets under different conditions of anticoagulation. Morphology is seen to be very well preserved, with integrity of all internal features maintained in regimes using both $Mg^{2+}$ and $Ca^{2+}$ as anticoagulant.

e.g. 250 mM $Mg^{2+}$: Blood anticoagulant ratio 9:1.
100 mM $Mg^{2+}$: Blood anticoagulant ratio 3:1.

This good preservation seems to be maintained for some days' storage under room temperature conditions, i.e. no detectable difference between electron micrographs prepared from platelets fixed immediately after separation from the blood and those prepared from platelets in platelet-rich plasma which have been maintained at room temperature for 24 hours and 3 days.

Functional tests on the platelets

There are various tests for metabolic and functional competence of which the commonest measure the capability of platelets to aggregate to each other following addition of a haemostatic agent to platelet-rich plasma (PRP). Agents usually used as ADP, Collagen, Thrombin, Arachidonic Acid, Adrenaline, etc. Early results with platelet-rich plasma prepared from Mg-anticoagulated blood (250 mM 1:9) showed that 1 mM ADP induced shape change (discs to spheres) but no aggregation. 10 mM ADP gave shape change and reversible aggregation.

The following studies were made with fresh platelets (within 1–2 hours of donation) anticoagulated by three regimes, citrate, heparin and $MgCl_2$ (250 mM), respectively.

The data refers to the lowest level of the agent required to produce full aggregation.

| Dates of assay | Citrated PRP | Heparinised PRP | $MgCl_2$ PRP |
|---|---|---|---|
| AGENT: ADP (All values μM) | | | |
| 3.2.83 | 1.0 | 0.5 | >20 |
| 9.2.83 | 1.4 | 0.4 | 40 |
| 16.2.83 | 1.2 | 0.5 | 40 |
| 23.2.83 | 1.0 | 0.5 | 40 |
| AGENT: COLLAGEN (All values μg/ml.) | | | |
| 3.2.83 | 0.4 | 0.4 | 5.0 |
| 9.2.83 | 0.4 | 1.0 | 4.0 |
| 16.2.83 | 0.7 | 0.4 | 5.0 |
| 23.2.83 | 0.4 | 0.4 | 3.0 |
| AGENT: ARACHIDONIC ACID (All values millimolar (mM)) | | | |
| 16.2.83 | 0.4 | 0.5 | — |
| 23.2.83 | 0.3 | 0.3 | 0.7 |
| 16.3.83 | 0.4* | 0.7* | 1.0+ |
| 23.3.83 | 0.4* | 0.7 | 0.6+ |

Some anomalous observations with respect to arachidonic acid appear in tests marked *: higher concentrations of the fatty acid gave full aggregation as expected but none were inhibitory to the tested limit 3 mM. With the $MgCl_2$ PRP, the test marked + showed inhibition of aggregation at 2–3 mM.

Some blood processing procedures to obtain blood products and derivatives from blood anticoagulated with neutral salts in accordance with the invention are as now described.

Procedure to isolate prothrombin and Factor VIII from mammalian blood plasma

Step 1

Venepuncture is performed in conventional way, draining blood into a two-bag Fenwell transfer pack containing magnesium chloride as the anti-coagulant. The blood is added to the anticoagulant to give a ratio of blood to anticoagulant of nine parts blood to one part anticoagulant or, preferably, three parts blood to one part anticoagulant: the initial concentration of the anticoagulant in each case is such as to give a final calculated concentration in the mixture of between 25 to 50 mM. Thus when nine parts blood are added to one part anticoagulant the latter has an initial concentration of 500 mM to give a final calculated concentration of $(1/10 \times 500 \text{ mM}) = 50$ mM $MgCl_2$, whereas if three parts blood are added to one part anticoagulant the latter is initially 200 mM to give a final calculated concentration of $(\frac{1}{4} \times 200 \text{ mM}) = 50$ mM $MgCl_2$ The three parts blood to one part anticoagulant ratio is preferred because the blood proteins are immediately diluted to a concentration at which their stability is enhanced and their subsequent separation (Step 5) is facilitated.

Step 2

The anticoagulated blood is centrifuged, in the conventional way, to separate the cells from the plasma. The supernatant plasma is then transferred to the second bag of the transfer pack.

Step 3

The plasma is diluted, if necessary, to give a final protein concentration of 2 gm per 100 ml, assuming an initial concentration of 8 gm per 100 ml. If the initial dilution of the blood with anticoagulant is three parts blood to one part anticoagulant, no further dilution is needed, at this step, whereas if the initial dilution of blood with anticoagulant is nine parts blood to one part anticoagulant, then at this step one volume of plasma is made up to a final volume of 3.6, using water as diluent.

The object of this dilution is to reduce the concentration of protein, firstly because of a concentration of 2 gm per 100 ml of the protein solution is more stable, and secondly because the subsequent electrophoretic separation procedure is more efficient when conducted with diluted plasma.

Step 4

The plasma is dialysed against a 8 mM solution of $MgCl_2$ in $H_2O$ to a conductivity approximately 2 millisiemans (mmho). Alternatively, the plasma may be dialysed against 2–6 mM $MgCl_2$ dissolved in a suitable buffer, such as Tris Glycine pH 7.4. An Amicon hollow fibre dialysis machine is used for the dialysis. The plasma is kept at constant volume and twice the volume of dialysis fluid, i.e. $MgCl_2$ in $H_2O$ or buffer, is added over a period of 24 hours.

The object of this dialysis is to remove sodium chloride from the plasma and so reduce the conductivity of the plasma to 2 mmho or less, which is a requirement for the continuous electrophoresis equipment used in Step 5 below.

Step 5

The diluted plasma, of conductivity 2 mmho or less, is now subjected to continuous electrophoresis, to fractionate the proteins into 29 receivers.

Step 6

Samples from each of the 29 receivers are first concentrated and then subjected to rocket immunoelectrophoresis, against antiprothrombin and antiFactor VIII, to locate the receivers containing these proteins.

Step 7

The receiver containing the Factor VIII is suitable for testing for its ability to correct the coagulant defect in haemophilia, and may subsequently be freeze dried for convenience of distribution for clinical use.

Step 7a

The contents of the receiver containing prothrombin are dialysed against physiological saline (140 mM NaCl) containing 8 mM $MgCl_2$ to give a solution of prothrombin containing 8 mM $MgCl_2$ and 140 mM NaCl.

Step 8

The solution of prothrombin obtained in Step 7a is first dialysed against 140 mM NaCl containing 8 mM $CaCl_2$ for 24 hours, against 140 mM and the NaCl containing 2 mM $CaCl_2$, thereby replacing the $Mg^{++}$ with $Ca^{++}$.

Step 9

This solution obtained in Step 8 is suitable for testing for its ability to correct the coagulant defect in haemophilia, and may subsequently be freeze dried for convenience of distribution for clinical use.

While the invention has been described in relation to the production of products from anticoagulated blood, it extends also to the production of products from anticoagulated bone marrow. Moreover, in addition to the blood products described, the invention may be applied especially to the production of immunoglobulins and complement, albumin and fibrinogen, growth factors and naturally-occurring mitogens.

We claim:

1. A process for the production of products for clinical use chosen from blood proteins, blood cells, plasma proteins, plasma cells, bone marrow proteins, or bone marrow cells comprising treating freshly shed blood or fresh bone marrow with an anticoagulant comprising a neutral salt which does not bind calcium ions, thereafter deriving said products for clinical use from the treated blood or marrow, and then reducing the toxicity of said products by removal of the ions of the salt below their toxic levels.

2. A process according to claim 1, wherein the anticoagulant natural salt contains at least one of the divalent ions calcium, magnesium, barium, or strontium.

3. A process according to claim 2, wherein the anticoagulant further comprises sodium and/or potassium ions.

4. A process according to claim 1, wherein the anticoagulant neutral salt is a magnesium salt in an amount corresponding to an 18 to 50 mM solution in the anticoagulated blood or marrow.

5. A process according to claim 4, wherein the anticoagulant further comprises sodium and/or potassium ions.

6. A process according to claim 4, wherein the anticoagulant is present in the anticoagulated blood in an amount corresponding to a 25 mM solution.

7. A process according to claim 1, wherein the anticoagulant is present in the anticoagulated blood in an amount corresponding to a 10 to 500 mM solution.

8. A process according to claim 7, wherein the anticoagulant is present in the anticoagulated blood in an amount corresponding to a 15 to 250 nM solution.

9. A process according to claim 8, wherein the anticoagulant is present in the anticoagulated blood in an amount corresponding to a 16 to 100 mM solution.

10. A process according to claim 1, wherein the anion of the neutral salt is chloride.

11. The process of claim 1 wherein the step of reducing the toxicity comprises contacting the treated blood or marrow with an ion exchange resin.

12. The process of claim 1 wherein the step of reducing the toxicity comprises dialyzing the blood or marrow.

13. The process of claim 1 as applied to blood comprising removing fresh blood from a mammalian donor into a blood pack container that is precharged with an aqueous solution of said neutral salt in appropriate amount.

14. The process of claim 1 as applied to blood comprising removing fresh blood from a mammalian donoer into a container containing a charge of a suitable amount, as compared with the blood being shed, of said neutral salt as a dry solid.

* * * * *